(12) United States Patent
Nakamura et al.

(10) Patent No.: US 7,883,687 B2
(45) Date of Patent: Feb. 8, 2011

(54) $^{15}$O-LABELED MONOSACCHARIDE AND PRODUCING METHOD THEREOF

(75) Inventors: Eiichi Nakamura, 5-3-3-1001, Honkomagome, Bunkyo-ku, Tokyo 113-0021 (JP); Shintaro Nishimura, Tokyo (JP); Yoshihiro Murakami, Tokyo (JP); Hideki Yorimitsu, Kyoto (JP)

(73) Assignees: Astellas Pharma Inc., Tokyo (JP); Eiichi Nakamura, Tokyo (JP)

( * ) Notice: Subject to any disclaimer, the term of this patent is extended or adjusted under 35 U.S.C. 154(b) by 991 days.

(21) Appl. No.: 11/579,330

(22) PCT Filed: Mar. 28, 2005

(86) PCT No.: PCT/JP2005/006547
§ 371 (c)(1), (2), (4) Date: Mar. 23, 2007

(87) PCT Pub. No.: WO2005/105708
PCT Pub. Date: Nov. 10, 2005

(65) Prior Publication Data
US 2007/0224120 A1    Sep. 27, 2007

Related U.S. Application Data

(60) Provisional application No. 60/566,921, filed on May 3, 2004.

(51) Int. Cl.
*A61M 36/14* (2006.01)
*A61K 51/00* (2006.01)
(52) U.S. Cl. .................. 424/1.73; 424/1.11
(58) Field of Classification Search ............... 424/1.11, 424/1.73, 1.85, 1.89; 549/354, 355, 542
See application file for complete search history.

(56) References Cited

U.S. PATENT DOCUMENTS 6,271,425 B1    8/2001  Nakamura et al.

FOREIGN PATENT DOCUMENTS

EP    0 588 480    3/1994

OTHER PUBLICATIONS

M. Af. Ugglas, et al., "Oxygen-15=Labeled Deoxyglucose for Positron-Camera Brain-Imaging", Annales Universitatis Turkuensis, Ser. D: Medical Application of Cgclotron, vol. 8, 1977, pp. 79-84.

*Primary Examiner*—Michael G Hartley
*Assistant Examiner*—Jagadishwar R Samala
(74) *Attorney, Agent, or Firm*—Oblon, Spivak, McClelland, Maier & Neustadt, L.L.P.

(57) ABSTRACT

This invention relates to novel $^{15}$O-labeled monosaccharide useful for positron emission tomography (PET) and producing method thereof.

12 Claims, 5 Drawing Sheets

$^{15}$O-LABELED MONOSACCHARIDE AND PRODUCING METHOD THEREOF

TECHNICAL FIELD

This invention relates to novel $^{15}$O-labeled monosaccharide useful for positron emission tomography (PET) and producing method thereof.

BACKGROUND ART

Positron emission tomography (PET) is a noninvasive bioimaging technology which can be used to diagnose functions or disorders of a variety of organs such as brain and heart. In PET, a radioactive tracer is administered to a subject to determine the distribution of the tracer in the body of the subject. To date, [$^{18}$F]2-fluoro-2-deoxyglucose (FDG) have been used as the most useful PET tracer. FDG can be used to determine sugar metabolism quantitatively and have lead to progressive improvement for brain study or cancer diagnosis. However, the number of times of PET measurement per one day is limited due to long half-life of $^{18}$F (110 min). Moreover, since $^{18}$F-labeled compound is non-natural, the behavior of $^{18}$F-labeled compound in a body is different from that of the corresponding natural compound. Further, although synthesis of glucose labeled with $^{15}$O at C1 position has been tried, such $^{15}$O-labeled glucose has been failed to be synthesized. Moreover, OH group at the C1 position of glucose molecule is unstable and easily subjected to exchange reaction with H$_2$O in blood. Therefore, such labeled glucose should not be suitable for PET measurement.

SUMMARY OF THE INVENTION

The present inventors have established novel $^{15}$O-labeled monosaccharide and producing method thereof to overcome such shortcomings of conventional labeled compounds for PET. The method for producing $^{15}$O-labeled monosaccharide of the present invention is partially based on the alcohol production method described in WO98/34893.

In one aspect, the present invention provides $^{15}$O-labeled monosaccharide which is labeled with $^{15}$O at hydroxymethyl group in the monosaccharide molecule.

In another aspect, the present invention provides a method for producing $^{15}$O-labeled monosaccharide, comprising reacting a monosaccharide, which is substituted with a halogen at hydroxyl of hydroxymethyl group in the monosaccharide molecule, with $^{15}$O oxygen in the presence of an organotin compound and a reducing agent, wherein said reacting occurs either in the absence of a radical initiator or in the presence of not more than 0.3 equivalent, based on the halogenated monosaccharide, of a radical initiator to provide $^{15}$O-labeled monosaccharide which is labeled with $^{15}$O at the hydroxymethyl group in the monosaccharide molecule.

In another aspect, the present invention provides a method for diagnosing a whole body, organs or tissues of a subject, comprising administering the above $^{15}$O-labeled monosaccharide to the subject to measure metabolism of the $^{15}$O-labeled monosaccharide in the subject.

In another aspect, the present invention provides a kit for producing $^{15}$O-labeled monosaccharide, comprising a monosaccharide which is substituted with a halogen at hydroxyl of hydroxymethyl group in the monosaccharide molecule, an organotin compound and a reducing agent, wherein the kit is used to react the halogenated monosaccharide with $^{15}$O oxygen in the presence of the organotin compound and the reducing agent to produce a $^{15}$O-labeled monosaccharide which is labeled with $^{15}$O at the hydroxymethyl group in the monosaccharide molecule.

The method of the invention can be used to produce $^{15}$O-labeled monosaccharide rapidly with high yield. Since $^{15}$O has short half-life (2 min), the $^{15}$O-labeled monosaccharide of the present invention can be used to practice more than once PET measurement per one day for a subject and with only little radioactive dose exposed to the subject. Moreover, the behavior of the $^{15}$O-labeled monosaccharide of the present invention in a body is more similar to that of natural compound than that of $^{18}$F-labeled compound. Further, since the $^{15}$O-labeled monosaccharide of the present invention is labeled with $^{15}$O at the hydroxymethyl group of the monosaccharide molecule (e.g., C6 position of hexose or C5 position of pentose), it is more stable in a body than monosaccharide labeled with $^{15}$O at C1 position. Therefore, the $^{15}$O-labeled monosaccharide of the present invention can be used in PET measurement to accomplish more successful imaging.

BRIEF DESCRIPTION OF THE DRAWINGS

FIG. 4 shows the results of PET scans for rat performed by using several of labeled compounds.

FIG. 5 shows the results of PET scans for mouse performed by using several of labeled compounds.

DETAILED DESCRIPTION OF THE PRESENT INVENTION

Figure 1:
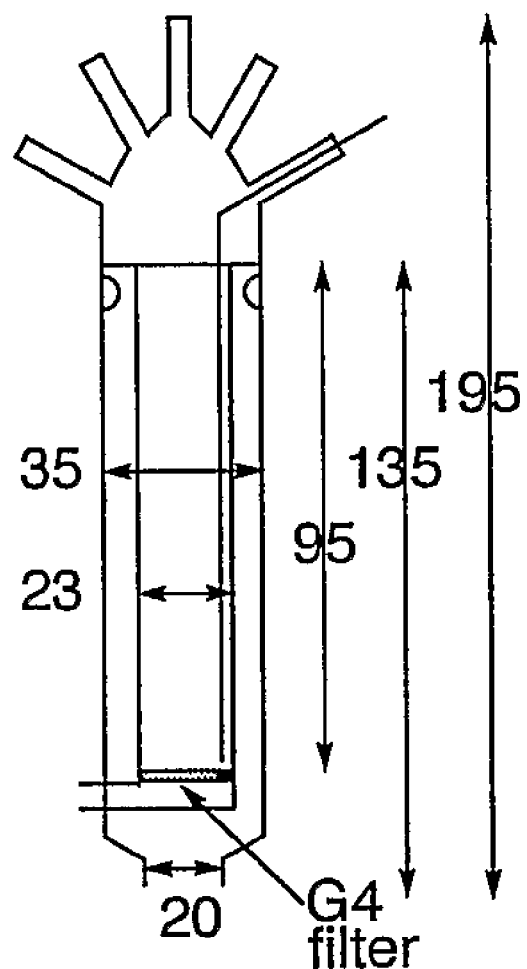
FIG. 1 shows the glass filter reactor used for radical hydroxylation of halogenated glucose in the Example. Numbers in this figure are length in mm.

The present invention is now described in detail.

The "monosaccharide" useful for the present invention includes any monosaccharide and derivative thereof known in the art. Preferably, the "monosaccharide" useful for the present invention is hexose or pentose. Hexose useful for the present invention includes D-glucose, D-galactose, D-mannose, D-fructose and derivative thereof. Pentose useful for the present invention includes D-xylose, D-ribose, D-deoxyribose, D-arabinose and derivative thereof. Preferably, the "monosaccharide" useful for the present invention is D-glucose or derivative thereof, and most preferably, D-glucose or 2-deoxy-D-glucose.

The term "labeled with $^{15}$O at hydroxymethyl group in the monosaccharide molecule" means that hydroxymethyl (—CH$_2$OH) group in the monosaccharide molecule is labeled with $^{15}$O to form —CH$_2$$^{15}$[O]H group. More specifically, the term means, for example, that if the monosaccharide is a hexose, the free hydroxyl on C6 carbon of the hexose is labeled with $^{15}$O, and that if the monosaccharide is a pentose, the free hydroxyl on C5 carbon of the pentose is labeled with $^{15}$O.

The "a monosaccharide which is substituted with a halogen" or "a halogenated monosaccharide" in the present invention is used as a precursor in the method for producing $^{15}$O-labeled monosaccharide of the present invention. Each of the terms is referred to a monosaccharide having a halogenated methyl group (—CH$_2$X, X is a halogen atom) formed by substituting a halogen for hydroxyl of hydroxymethyl group in the monosaccharide molecule.

The "halogen" in the halogenated monosaccharide to be used in the present invention includes chloro, iodo, bromo and so on, iodo is the most preferred halogen for purposes of the invention.

The "organotin compound" useful for the present invention includes, but is not limited to, organotin hydrides (e.g., trialkyltin hydrides and triaryltin hydrides) and organotin halides (e.g., tributyltin chloride, dibutyl(t-butyl)tin chloride and triaryltin halides (e.g. triphenyltin chloride)). Preferably, organotin compound includes trialkyltin hydrides. Most preferable organotin compound is tributyltin hydrides.

The amount of the organotin compound to be used in the present invention may be a catalyst amount, is preferably 1.0-6.0 equivalents, and more preferably 2.0-5.0 equivalents, based on the substrate halogenated monosaccharide.

The "reducing agent" useful for the present invention includes, but is not limited to, reducing agents known in the art such as phosphine, sulfide, selenide, telluride, arsine, stibane, bismuthane or derivative thereof, borohydrides. Preferred reducing agent for use in the present invention is triphenylphosphine.

The amount of the reducing agent to be used in the present invention is sufficient for reducing peroxide produced in the reaction, and preferably at least 1 equivalent based on the substrate halogenated monosaccharide.

The reaction according to the present invention can be carried out using various solvents which do not interfere with the reaction. Such solvent includes fluorine-solvent (e.g., benzofluoride, benzotrifluoride, perfluorodecalin, etc.), alcohol (e.g. ethanol, isopropyl alcohol, butanol, t-butanol, etc.), BTX, and ethers (e.g. tetrahydrofuran etc.), inclusive of mixtures thereof, among others. Those skilled in the art can select suitable solvent for the reaction based on, for example, solubility of the halogenated monosaccharide or $^{15}$O oxygen in the reaction system. Preferred solvent is a mixture of fluorine-solvent and alcohol.

The reaction temperature for use in the present invention is not particularly restricted provided that the radical reaction is enabled to proceed, although the reaction is preferably conducted at not less than 50° C., and more preferably 75-85° C.

Figure 3:
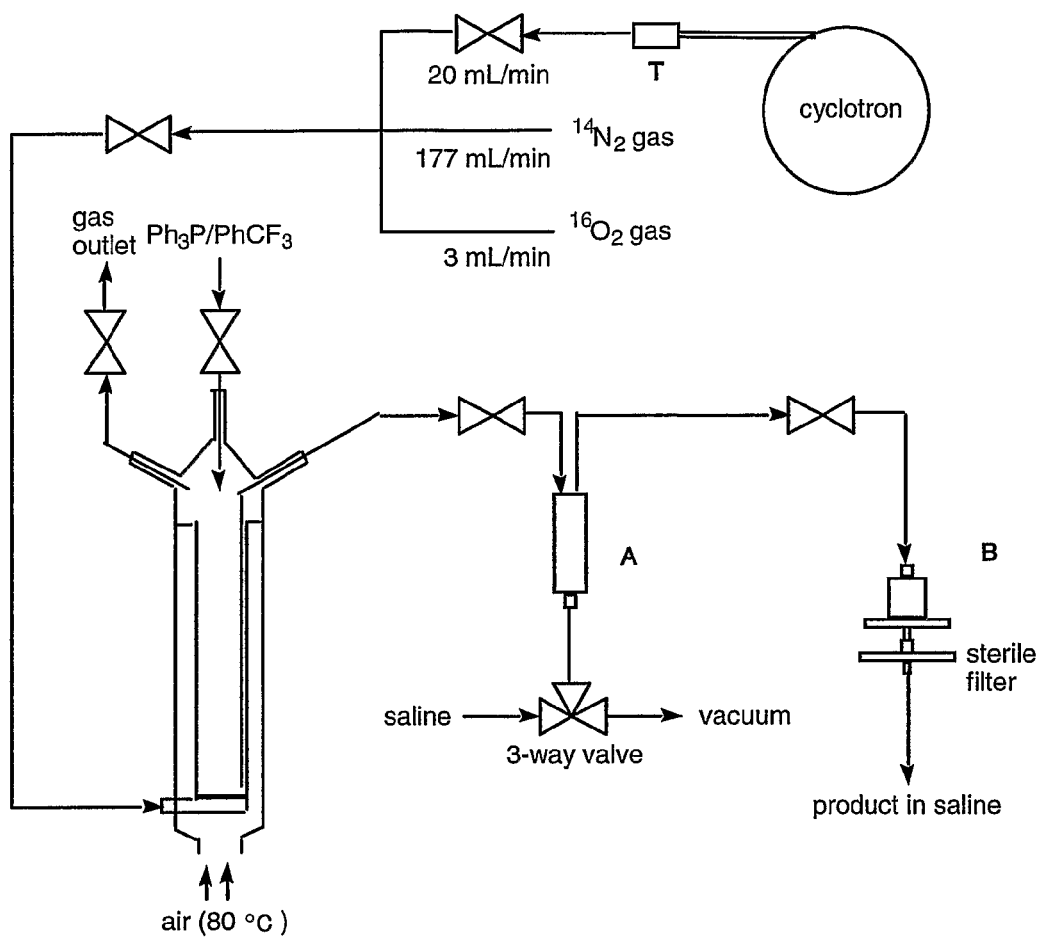
FIG. 3 shows the cyclotron system used for generation of $^{15}$O oxygen and introduction of it into the reaction system.

$^{15}$O oxygen used in the present invention can be produced, for example, by generating the nuclear reaction $^{15}$N(p, n)$^{15}$O by proton bombardment from a cyclotron on target gas containing $^{16}$O$_2$ and $^{15}$N$_2$, or by generating the nuclear reaction $^{15}$N(d, n) $^{15}$O by deuteron bombardment from a cyclotron on target gas containing $^{16}$O$_2$ and $^{15}$N$_2$. Then the target gas containing $^{15}$O oxygen produced is mixed with cold carrier gas and introduced into the reaction system (FIG. 3).

Preferably, prior to introduction of $^{15}$O oxygen in the reaction system, carrier gas containing oxygen ($^{16}$O$_2$) is introduced into the reaction system to initiate radical reaction. Preferably, the initiation of the radical reaction is monitored, and the introduction of $^{15}$O oxygen into the reaction system is started simultaneously with the initiation of the radical reaction. The initiation of the radical reaction can be easily monitored by those skilled in the art using an analytical technique (e.g., TLC) known in the art Concentration of $^{16}$O$_2$ in the cold carrier gas introduced into the reaction system to initiate radical reaction is preferably at least 1.5% and more preferably 1.5%-5.0%, although the concentration is suitably adjusted by those skilled in the art based on, for example, reaction conditions such as induction time of the radical reaction. Concentration of $^{16}$O$_2$ in the target gas is preferably equivalent to the concentration of $^{16}$O$_2$ in the cold carrier gas, although it is suitably adjusted by those skilled in the art based on, for example, yield of $^{15}$O-labeled monosaccharide produced.

In the method for producing $^{15}$O-labeled monosaccharide of the present invention, the radical reaction can be caused without substantially using "radical initiator". However, "radical initiator" may be introduced into the reaction system for promoting the reaction or for suppressing production of reductants as byproduct. If "radical initiator" is used in the method of the present invention, the amount of the "radical initiator" is preferably no more than 0.3 equivalents and more preferably no more than 0.03 equivalents, based on the halogenated monosaccharide.

The "radical initiator" for use in the present invention includes, but is not limited, to AIBN and dibenzoyl peroxide.

The method for producing $^{15}$O-labeled monosaccharide of the present invention can be carried out by using any reaction vessel known in the art or an reaction vessel which those skilled in the art can easily make using any experimental appliance known in the art (e.g., glass filter). For example, a preferred reaction vessel useful for the method of the present invention is a reaction vessel comprising a glass filter at the bottom as shown in the following examples, wherein $^{15}$O oxygen in the mixed gas can bubble very finely in the reaction vessel. Such reaction vessel can be made by those skilled in the art referring the teaching of the specification. Preferably, the reaction vessel has longitudinally long form for dissolving sufficient $^{15}$O oxygen in the reaction system.

The kit for producing $^{15}$O-labeled monosaccharide of the present invention comprises a halogenated monosaccharide, an organotin compound and a reducing agent, wherein the kit is used to react the halogenated monosaccharide with $^{15}$O oxygen in the presence of the organotin compound and the reducing agent to produce $^{15}$O-labeled monosaccharide of the present invention. The $^{15}$O oxygen can be supplied from, for example, a cyclotron equipped in an institution (e.g., a hospital) wherein a diagnosis of a subject is practiced. Preferably, the kit of the present invention further comprise no more than 0.3 equivalents, based on the halogenated monosaccharide, of radical initiator. In one embodiment, the kit of the present invention further comprises a reaction vessel in which the reaction can be practiced to produce $^{15}$O-labeled monosaccharide. Preferably, the reaction vessel may be a vessel in a disposable cassette format known in the art to be able to produce $^{15}$O-labeled monosaccharide easily and rapidly.

The $^{15}$O-labeled monosaccharide of the present invention can be used to diagnose a whole body, organs or tissues of a subject. The diagnosing method comprises administering the $^{15}$O-labeled monosaccharide of the present invention to the subject to measure metabolism of the $^{15}$O-labeled monosaccharide in the subject. Such measurement can be carried out by using any medical imaging method known in the art such as positron emission tomography. The organ or tissue diagnosed by using the $^{15}$O-labeled monosaccharide of the present invention includes, but is not to be limited, brain, heart or tumor tissue which metabolizes glucose actively. Further, due to much shorter half-life of $^{15}$O than that of $^{18}$F, the $^{15}$O-labeled monosaccharide of the present invention can be used to measure diurnal variation of sugar metabolism in one subject over time.

If the $^{15}$O-labeled monosaccharide of the present invention is used as a diagnostic agent, the reaction product is preferably purified to remove the organotin compound and the reducing agent in the reaction mixture. Such purification method includes, but is not to be limited, solid-phase extraction using silica gel column (e.g., Sep-Pak C18) and HPLC.

The reaction conditions of the present invention have been described above. In conducting a specific reaction, it is necessary to optimize the reaction conditions according to the structure of the halogenated monosaccharide and the species and amount of the organotin compound, among other variables, but such optimization is a matter which can be made easily by anyone skilled in the art. Further, the method for producing $^{15}$O-labeled monosaccharide of the present invention is applicable to disaccharide (e.g., maltose, sucrose, lactose) and oligosaccharide provided that the saccharides have a free hydroxyl group on C6 carbon of hexose residue or C5 carbon of pentose residue in the molecule.

The following examples illustrate the present invention in further detail.

EXAMPLE

Materials

Unless otherwise noted, chemicals were used as they are.

2-Butanol (Kanto Chemical) was distilled from CaH$_2$ prior to use. Benzotrifluoride, perfluorodecalin and AIBN were purchased from Acros, Fluorochem Ltd. and Wako Pure Chemicals, respectively. n-Bu$_3$SnH was obtained from Aldrich and used without further purification. N$_2$/O$_2$ gas (98.5/1.5) was obtained from Nippon Sanso Co., Ltd.

Equipments

Hydroxylation of 2,6-dideoxy-6-iodo-D-glucose and 6-iodo-6-deoxy-D-glucose was performed in the glass filter reactor as shown in FIG. 1. Sep-Pak cartridges were purchased from Waters. The cyclotron is OSCAR-12 (NKK/Oxford). The target gas consisted of 1.5% O$_2$ in $^{15}$N$_2$. PET scans were obtained on Planar Positron Imaging System (Hamamatsu Photonics K.K.).

Example 1

Synthesis of 2,6-dideoxy-6-iodo-D-glucose

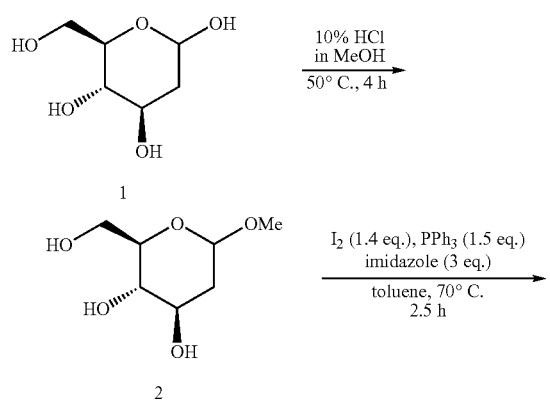

2-deoxy-D-glucose (1) (Aldrich) (5.0 g, 30 mmol) was placed in a flask, and HCl solution in methanol (10%, 60 ml) was added. The resulting mixture was heated at 50° C. overnight. After cooling to room temperature, silver carbonate was added, and the mixture was vigorously stirred by when generation of CO$_2$ gas have finished. The reaction mixture was filtrated through Celite, and the resultant solution was evaporated. Toluene (20 ml) was added to the solution, and the resultant mixture was evaporated to remove the residual methanol. Toluene (250 ml) was added and dissolved in the concentrated residue, and imidazole (6.12 g, 90.0 mmol), triphenylphosphine (11.8 g, 45.0 mmol) and iodine (11.5 g, 42.0 mmol) were added. Again, toluene (200 ml) was added, and the resultant mixture was vigorously stirred under N$_2$ flow at 70° C. for 2.5 h. After the reaction completed, the supernatant in the reaction vessel was transferred to another vessel and evaporated. On the other hand, chloroform was added to the gummy solid component in the reaction vessel to give a suspension, and the suspension was filtrated through Celite. The filtrate was evaporated and combined to the concentrated supernatant solution obtained previously. The combined solution was subjected to column chromatography (chloroform:methanol=20:1, twice) to afford 5.9 g of compound 3. The yield is 68% based on compound 1.

Compound 3 (5.9 g) was placed in a flask, and sulfuric acid (0.5 M aqueous solution, 200 ml) was added. The solution was stirred at 80° C. for 1.5 h. After cooling to room temperature, sodium hydrogencarbonate was carefully added portionwise to the acidic solution to neutralize it. The resultant mixture was then directly evaporated (bath temp. no more than 40° C.). The evaporation was stopped when the volume of the solution reduced to about 10-20 ml. Methanol (100 ml) was added to the resultant concentrated solution, which led to growth white solid of sodium sulfate. The solution was filtrate through Celite, and the filtrate was evaporated at no more than 30° C. The concentrated residue was subjected to column chromatography (chloroform:methanol=8:1) repeatedly to afford 4.2 g of 2,6-dideoxy-6-iodo-D-glucose (compound 4). The yield is 51% based on compound 1.

Example 2

Synthesis of 6-iodo-6-deoxy-D-glucose

D-Glucose  1) TsCl (1.0 eq) pyridine (300 ml)
2) AC$_2$O (80 ml)

column purification (chloroform:methanol=3:1) afforded 6-deoxy-6-iodo-D-glucose (compound 7) (2.16 g g, 7.44 mmol, 50%).

Example 3

Radical Hydroxylation of 2,6-dideoxy-6-iodo-D-glucose in the Glass Filter Reactor (1)

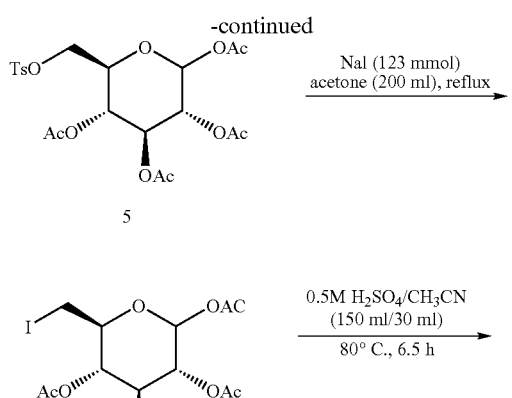

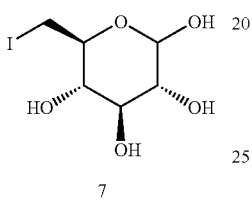

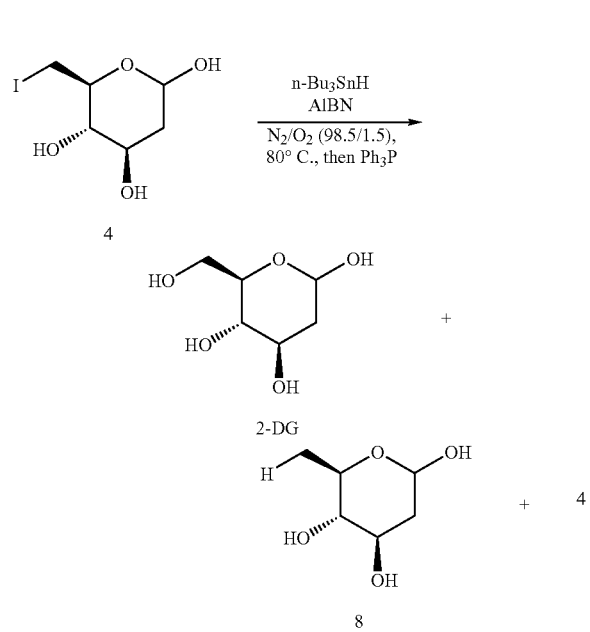

D-Glucose (20.0 g, 0.111 mol) was placed in a 1000-mL round-bottomed flask, and pyridine (300 ml) was added. Some of glucose remained undissolved. p-Toluensulfonyl chloride (22.0 g, 0.115 mol) was added at ambient temperature. After stirring for 11 h, acetic anhydride (80 ml, 0.83 mol) was added in one portion. Gentle exothermic reaction took place. After being stirred for 1.5 h, the mixture was evaporated. Ethanol (200 ml) was added to a residual oil. The oil was dissolved and soon a white crystal appeared. After the mixture stood undisturbed at −10° C. for 27 h, the crystal was collected on a glass filter, washed with cold ethanol (25 ml, twice), and dried under reduced pressure. 6-O-(p-Toluenesulfonyl)-1,2,3,4-tetra-O-acetyl-β-D-glucose (compound 5) was obtained in 33% yield (18.5 g, 36.8 mmol).

6-O-(p-Toluenesulfonyl)-1,2,3,4-tetra-O-acetyl-β-D-glucose (5, 18.5 g, 36.8 mmol) was place in a 500-mL round-bottomed flask. Acetone (200 ml) and sodium iodide (18.5 g, 123 mmol) were added. The resulting mixture was heated at reflux for 20 h. The reaction proceeded gradually. The mixture was poured into 1000 ml of water, and the resulting solid was filtered with a glass filter. Recrystalization from ethanol afforded 6-deoxy-6-iodo-1,2,3,4-tetra-O-acetyl-β-D-glucose (compound 6) in 65% yield (11.0 g, 24.0 mmol).

6-Deoxy-6-iodo-1,2,3,4-tetra-O-acetyl-β-D-glucose (6, 6.87 g, 15.0 mmol) was placed in a 500-mL round-bottomed flask. Sulfuric acid (0.5 M aqueous solution, 150 ml) and acetonitrile (30 ml) were added to 6, and the mixture was heated at 80° C. for 6.5 h. After cooling to room temperature, sodium hydrogecarbonate was carefully added portionwise to the acidic solution. Neutralization was checked with indicator paper, and the mixture was then directly evaporated (bath temp. 40° C.). Before complete removal of solvent (ca. 10-20 ml), methanol (100 ml) was added to the flask, which led to growth of white precipitate. Filtration through Celite, concentration of the filtrate (bath temp. 30° C.), and silica gel 2,6-dideoxy-6-iodo-D-glucose (4) (162 mg, 0.600 mmol) as obtained in Example 1 and AIBN (2.4 mg, 0.015 mmol) were placed in a 20-mL vial. 2-Butanol (1.8 ml) was added, and 4 was dissolved. Benzotrifluoride (12.0 ml) and perfluorodecalin (2.7 ml) were then added. Tributyltin hydride (485 µl, 1.80 mmol) was introduced by a microsyringe. Note that addition by a normal syringe may cause initiation of the reaction before bubbling, giving only compound 8. The homogeneous solution was transferred with a Pasteur pipette into the glass filter reactor. The reactor was then immersed in an oil bath (80° C.) with bubbling of mixed gas ($N_2/O_2$=98.5/ 1.5, 200 ml/min). The glass filter made very fine bubbles. TLC analyses were done every 30 sec, which indicated that the reaction actually started at 1.5 min and completed at 4.0 min after the heating started. After 7.0 min, the reaction mixture was transferred to a solution of triphenylphosphine (157 mg, 0.600 mmol) in toluene (1.5 ml). The reactor was rinsed with 10 ml of methanol once. Concentration under reduced pressure afforded a mixture of oil and viscous residue. Toluene (10 ml) was added, and the resulting supernatant was passed through a Sep-Pak Cartridge silica (long body, conditioned with 10 ml of toluene prior to use). Here the gummy residue, which consisted of glycosides, was not soluble in toluene. The eluent containing tin and phosphine compounds was thrown away. Again, toluene was added to the gummy residue, and the toluene layer was passed through the same cartridge. The cartridge was then washed with methanol (5 ml+5 ml) by using the same syringe that was employed to take up the toluene solutions. The methanolic eluent was added the gummy glycosides. Evaporation and $^1$H NMR measurement (1,1,2,2-tetrachloromethane as an internal standard) revealed that the mixture consisted of 0.182 mmol (31% based on 4, 54% based on $O_2$ that passed through the solution during the radical chain) of 2-deoxy-D-glucose (2-DG) and 0.402 mmol (67%) of 8, in addition to a trace of tin and phosphine impurities.

Example 4

Radical Hydroxylation of 2,6-dideoxy-6-iodo-D-glucose in the Glass Filter Reactor (2)

The method used in this example was substantially same as the method shown in the above Example 3. A mixture of 4 (270 mg, 1.0 mmol), tributyltin hydride (3.0 mmol) and AIBN (0.025 mmol) in α,α,α,-trifluorotoluene (20.0 ml)/perfluorodecalin (4.5 ml)/2-butanol (3.0 ml) was heated at 80° C. with concomitant bubbling of $N_2/O_2$ (98.5/1.5, 180 ml/min for 0 to 2 min 40 sec, 200 ml/min for 2 min 40 sec to 6 min 20 sec). TLC analyses were done every 30 sec, which indicated that the reaction actually started at 3 min 20 sec and completed at 6.5 min after the heating started. After 7.0 min, workup with triphenylphosphine (1.0 mmol) reduced hydroperoxide into 2-DG. $^1$H NMR measurement revealed that the mixture consisted of 0.280 mmol (28% based on 4, 70% based on $O_2$ that passed through the solution during the radical chain) of 2-DG and 0.72 mmol (72%) of 8, in addition to a trace of tin and phosphine impurities.

Example 5

Radical Hydroxylation of 6-iodo-6-deoxy-D-Glucose in the Glass Filter Reactor

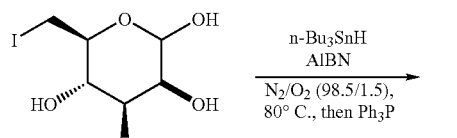

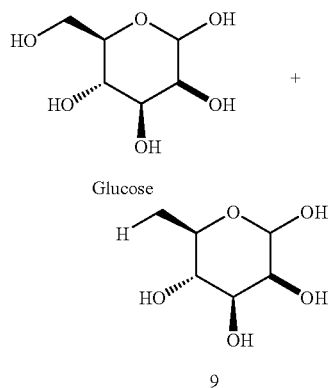

6 iodo-6-deoxy-D-glucose (7) (261 mg, 0.900 mmol) as obtained in Example 2 and AIBN (3.6 mg, 0.015 mmol) were placed in a 20-mL vial. 2-Butanol (3.5 ml) was added, and 7 was dissolved. Benzotrifluoride (15.0 ml) and perfluorodecalin (2.0 ml) were then added. Tributyltin hydride (484 μml, 1.80 mmol) was introduced by a microsyringe. The homogeneous solution was transferred with a Pasteur pipette into the glass filter reactor. The reactor was then immersed in an oil bath (80° C.) with bubbling of mixed gas ($N_2/O_2$=98.5/1.5, 200 ml/min). TLC analyses were done every 30 sec, which indicated that the reaction actually started at 2.0 min and completed at 5.0 min after the heating started. After 7.0 min, the reaction mixture was transferred to a solution of triphenylphosphine (236 mg, 0.900 mmol) in toluene (2.0 ml). The reactor was rinsed with 10 ml of methanol twice. Workup, purification, and NMR analysis as shown in Example 3 revealed that the mixture consisted of 0.198 mmol (22% based on 7, 50% based on $O_2$ that passed through the solution during the radical chain) of glucose, 0.569 mmol (63%) of 9 and 0.137 mmol (15%) of 7 in addition to a trace of tin and phosphine impurities.

Example 6

Figure 2:
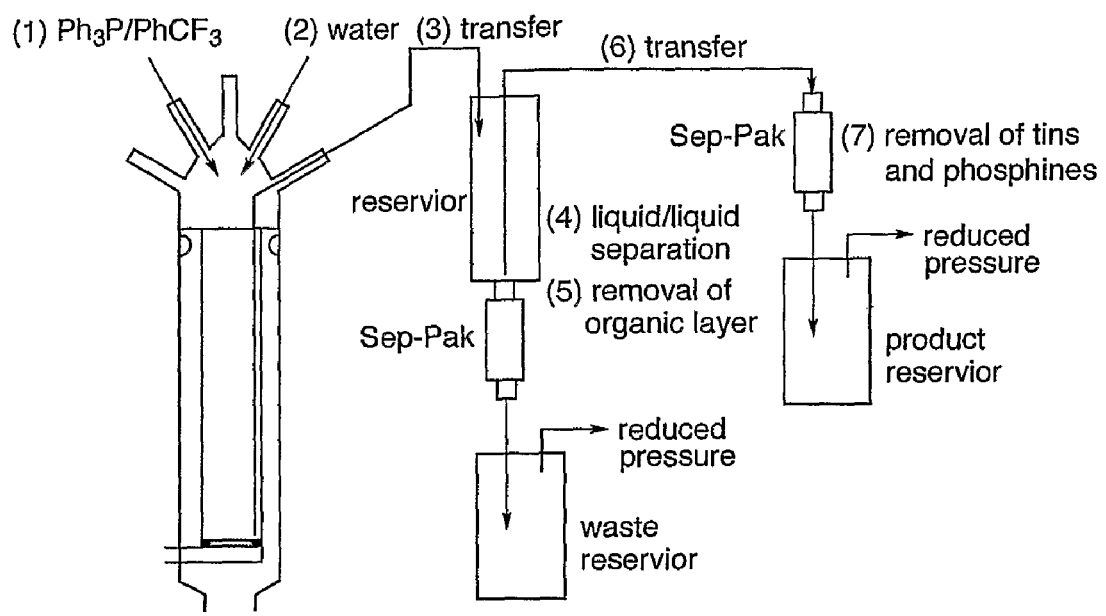
FIG. 2 shows the purification system used for purification of $^{15}$[O]2-deoxy-D-glucose.

Hydroxylation of 2,6-dideoxy-6-iodo-D-glucose in the Glass Filter Reactor followed by Rapid Purification For administration to an animal, the produced 2-DG is necessary to be separated from tin-compound and phosphine-compound. Therefore, the present inventors constructed a purification system as shown in FIG. 2 and purified the produced 2-DG by using the system.

After the reaction was performed for 4 min as shown in Example 3, triphenylphosphine (157 mg, 0.600 mmol in 2 mL of $PhCF_3$) was added to the reaction mixture, and bubbling continued for 10 sec. Water (3 ml) was added, and bubbling continued for 20 sec. The whole mixture was transferred to a reservoir and then stood undisturbed for 20 sec to float an aqueous layer (ca. 2.3 ml) on a fluorous organic layer. The lower layer was eluted away through a Sep-Pak C18 cartridge (conditioned with 10 ml of $PhCF_3$) by using a reduced pressure. The elution stopped at the boundary of the two layers. The aqueous layer on the top of the cartridge was then passed through another Sep-Pak C18 cartridge (conditioned with 10 ml of methanol and then with 10 ml of water). The eluate was a tin- and phosphine-free aqueous solution of 2-DG (17%, 0.103 mmol), 4 (trace) and 8 (47%, 0.280 mmol).

Example 7

PET Imaging Using $^{15}$[O]2-deoxy-D-glucose

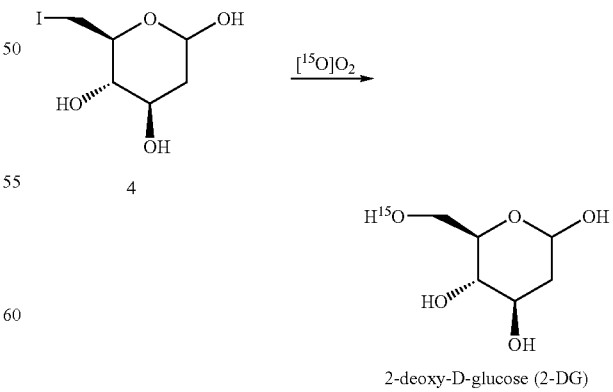

A solution of 2,6-dideoxy-6-iodo-D-glucose (274 mg, 1.0 mmol), tributyltin hydride (807 μl, 3.0 mmol) and AIBN (4.0 mg, 0.025 mmol) in $PhCF_3$ (20.0 ml)/$C_{10}F_{18}$ (4.5 ml)/2-

BuOH (3.0 ml) was placed in the reactor, which was on the automated synthetic apparatus (FIG. 3). Proton bombardment (beam current 50 μA) on target gas started ($N_2/O_2$=98.5/1.5, target gas pressure=6 kg/cm$^2$). The beginning of the bombardment was defined as 0 sec for convenience. Cold gas ($N_2/O_2$=1773/3, 180 ml/min) was provided and heating with temperature-controlled air (80° C.) started simultaneously at 2 min 40 sec. At 4.0 min, the target gas was evacuated from the targeting area in the cyclotron system (20 ml/min). The target gas was mixed with cold $N_2/O_2$ gas (target gas/$N_2/O_2$=20/177/3, 200 ml/min), and the resulting gas was then supplied to the reaction vessel. At 4 min 40 sec, the RI counter at the detector indicated arrival of hot gas. At 5 min 20 sec, the bombardment stopped. However, evacuation of the target gas continued. Triphenylphosphine (262 mg, 1.0 mmol in 1.5 ml of PhCF$_3$) was added at 6.0 min. At 6 min 10 sec, all the mixture was transferred from the reactor to a Sep-Pak Vac Silica cartridge (conditioned with 10 ml of PhCF$_3$) (A in FIG. 3) and the eluent was removed. Saline (3.0 ml) was consequently passed through the Sep-Pak Vac Silica cartridge. The eluted aqueous solution was passed through Sep-Pak C18 cartridge (conditioned with 10 ml of acetonitrile and then with 10 ml of saline) (B in FIG. 3) and afforded to a tin- and phosphine-free aqueous solution of $^{15}$[O]2-deoxy-D-glucose ([$^{15}$O]2-DG) (ca. 3 ml, 15-20 mCi).

Figure 4A:
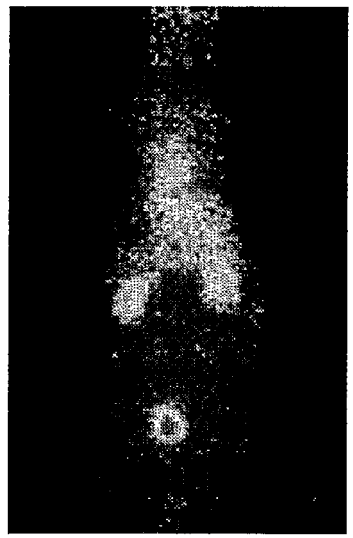
FIGS. 4A and 4B show integrated PET image from 15 min to 30 min after administration of $^{15}$[O]2-deoxy-D-glucose and $^{18}$[F]FDG, respectively.
Figure 4B:
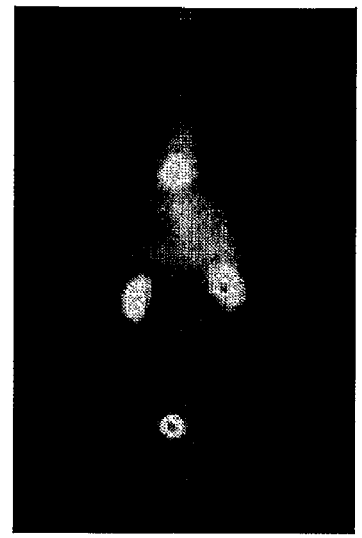
Figure 4C:
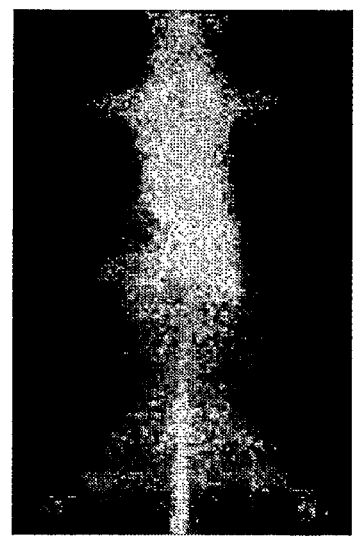
FIGS. 4C and 4D show PET image of initial blood flow from 0 sec to 90 sec and from 15 min to 30 min after administration of [$^{15}$O]H$_2$O, respectively.
Figure 4D:
Figure 5A:
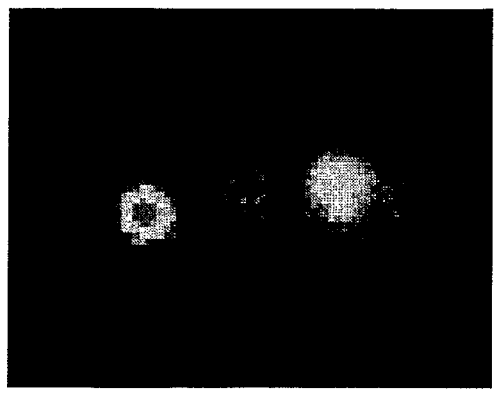
FIGS. 5A and 5B show integrated PET image from 15 min to 30 min after administration of $^{15}$[O]2-deoxy-D-glucose and $^{18}$[F]FDG, respectively.
Figure 5B:
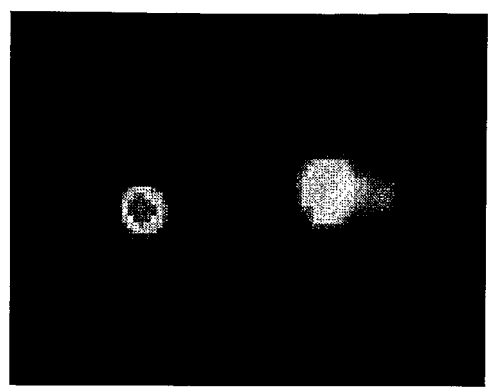
Figure 5C:
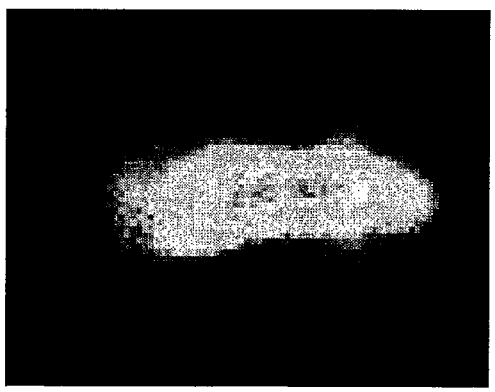
FIGS. 5C and 5D show PET image of initial blood flow from 0 sec to 90 sec and from 15 min to 30 min after administration of [$^{15}$O]H$_2$O, respectively.
Figure 5D:
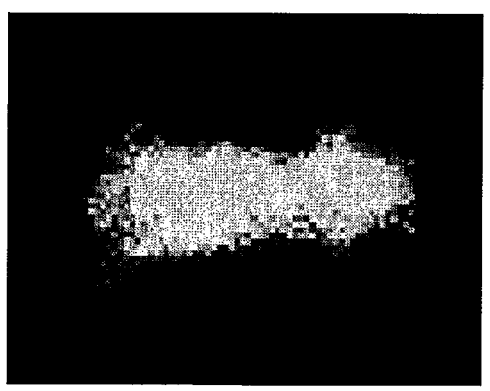

For rat imaging, 1 mL of the [$^{15}$O]2-DG solution was injected from his tail vein. [$^{15}$O]2-DG-PET scans could be performed over 30 min after the administration. Integrated PET image from 15 min to 30 min appeared accumulation of [$^{15}$O]2-DG in heart, kidney and bladder (FIG. 4A). For comparison with [$^{15}$O]2-DG, [$^{18}$F]FDG-PET scans were also performed, and integrated PET image for same period appeared accumulation of [$^{18}$F]FDG-PET like that of [$^{15}$O]2-DG (FIG. 4B). These images were clearly different from the image of initial blood flow from 0 sec to 90 sec (FIG. 4C) and from 15 min to 30 min (FIG. 4D) of [$^{15}$O]H$_2$O. Similar results were also obtained for mouse imaging (FIG. 5). These results proves that [$^{15}$O]2-DG can be used as a PET tracer like [$^{18}$F]FDG.

The invention claimed is:

1. A $^{15}$O-labeled monosaccharide which is labeled with $^{15}$O at hydroxymethyl group in the monosaccharide molecule wherein the monosaccharide is hexose or pentose.

2. The $^{15}$O-labeled monosaccharide of claim 1, wherein the monosaccharide is D-glucose or 2-deoxy-D-glucose.

3. A method for producing $^{15}$O-labeled monosaccharide wherein the monosaccharide is hexose or pentose, comprising reacting the monosaccharide, which is substituted with a halogen at hydroxyl of hydroxymethyl group in the monosaccharide molecule, with $^{15}$O oxygen in the presence of an organotin compound and a reducing agent, wherein said reacting occurs either in the absence of a radical initiator or in the presence of not more than 0.3 equivalent, based on the halogenated monosaccharide, of a radical initiator to provide $^{15}$O-labeled monosaccharide which is labeled with $^{15}$O at the hydroxymethyl group in the monosaccharide molecule.

4. The method of claim 3, wherein the monosaccharide is D-glucose or 2-deoxy-D-glucose.

5. The method of claim 3, wherein the halogen is iodo.

6. The method of claim 3, wherein the amount of the organotin compound is 2.0-5.0 equivalents based on the halogenated monosaccharide.

7. The method of claim 3, wherein the organotin compound is an organotin hydride.

8. The method of claim 7, wherein the organotin compound is trialkyltin hydrides.

9. The method of claim 3, wherein the reducing agent is a phosphine.

10. The method of claim 9, wherein the reducing agent is triphenylphosphine.

11. The method of claim 3, wherein in the reacting step, gas containing $^{16}$O is introduced into the reaction to initiate radical reaction prior to introduction of the $^{15}$O oxygen.

12. The method of claim 11, wherein the amount of $^{16}$O$_2$ in the gas is at least 1.5%.

* * * * *